(12) United States Patent
Ducker et al.

(10) Patent No.: US 6,913,718 B2
(45) Date of Patent: Jul. 5, 2005

(54) METHOD OF MAKING SHAPED COMPONENTS FOR DISPOSABLE ABSORBENT ARTICLES

(75) Inventors: Paul Ducker, St. Simons, GA (US); Rangachari Krishnakumar, Savannah, GA (US)

(73) Assignee: Rayonier Products & Financial Services Company, Fernandina Beach, FL (US)

( * ) Notice: Subject to any disclaimer, the term of this patent is extended or adjusted under 35 U.S.C. 154(b) by 54 days.

(21) Appl. No.: 10/011,513

(22) Filed: Nov. 5, 2001

(65) Prior Publication Data

US 2003/0087056 A1 May 8, 2003

(51) Int. Cl.[7] .............................................. B32B 31/00
(52) U.S. Cl. .................... 264/37.1; 264/37.28; 264/138; 264/146; 264/147; 264/157; 264/160; 428/80; 442/413
(58) Field of Search .......................... 264/37.1, 37.28, 264/138, 146, 147, 157; 428/80; 442/413

(56) References Cited

U.S. PATENT DOCUMENTS

| | | |
|---|---|---|
| 1,172,067 A | 2/1916 | Spiegel |
| 1,179,493 A | 4/1916 | Ball |
| 3,192,927 A | 7/1965 | Chauviere |
| 3,623,927 A | 11/1971 | Watson |
| 3,805,790 A | 4/1974 | Kaczmarzyk et al. |
| 3,860,003 A | 1/1975 | Buell |
| 3,875,837 A | 4/1975 | Dussaud |
| 4,670,960 A | 6/1987 | Provost |
| 4,690,719 A | 9/1987 | Lucas et al. |
| 4,695,278 A | 9/1987 | Lawson |
| 4,760,764 A | 8/1988 | De Jonckheere et al. |
| 4,862,574 A | 9/1989 | Seidy |
| 5,034,007 A | 7/1991 | Igaue et al. |
| 5,110,386 A | 5/1992 | Ochi et al. |
| 5,294,478 A | 3/1994 | Wanek et al. |
| 5,399,219 A | 3/1995 | Roessler et al. |
| 5,490,846 A | 2/1996 | Ellis et al. |
| 5,580,411 A | 12/1996 | Nease et al. |
| 5,597,437 A | 1/1997 | Lange et al. |
| 5,695,846 A | 12/1997 | Lange et al. |
| 6,171,432 B1 | 1/2001 | Brisebois et al. |

FOREIGN PATENT DOCUMENTS

| | | |
|---|---|---|
| EP | 0 670 153 A1 | 6/1995 |
| WO | WO 98/29070 | 7/1998 |

*Primary Examiner*—Elizabeth M. Cole
(74) *Attorney, Agent, or Firm*—Wood, Phillips, Katz, Clark & Mortimer

(57) ABSTRACT

A method for formation of shaped components such as shaped absorbent cores, for disposable absorbent articles, contemplates that a relatively wide web of material be provided from which the components are cut. The web of material is longitudinally slit to form a plurality of subdivided webs each having shaped components arranged in serial relationship. The shaped components of adjacent ones of the subdivided webs are nested with each other, that is, a line extending longitudinally of the web extends through the components of adjacent subdivided webs. Efficient formation is facilitated by collecting the marginal portions of the web of material, and at least partially recycling the collected portions for formation of the wide web.

8 Claims, 3 Drawing Sheets

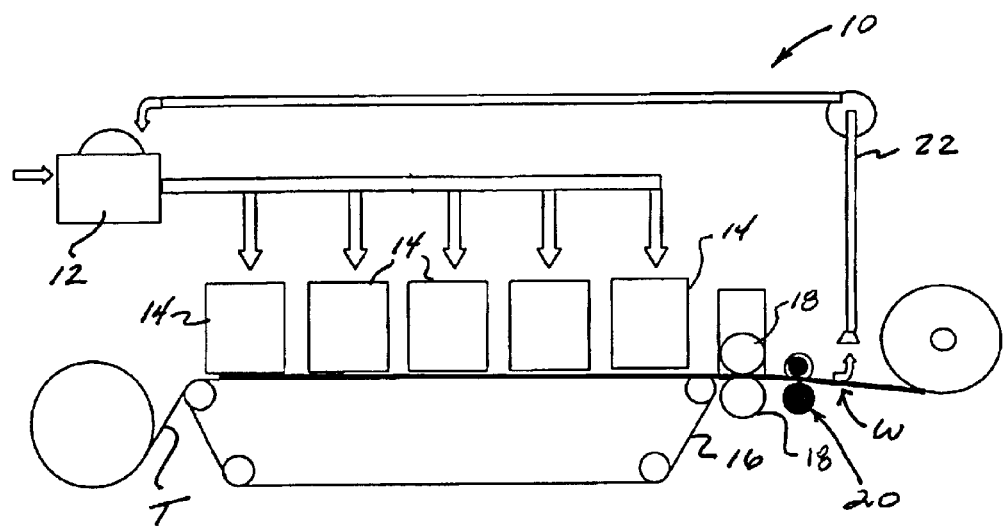
FIG_1
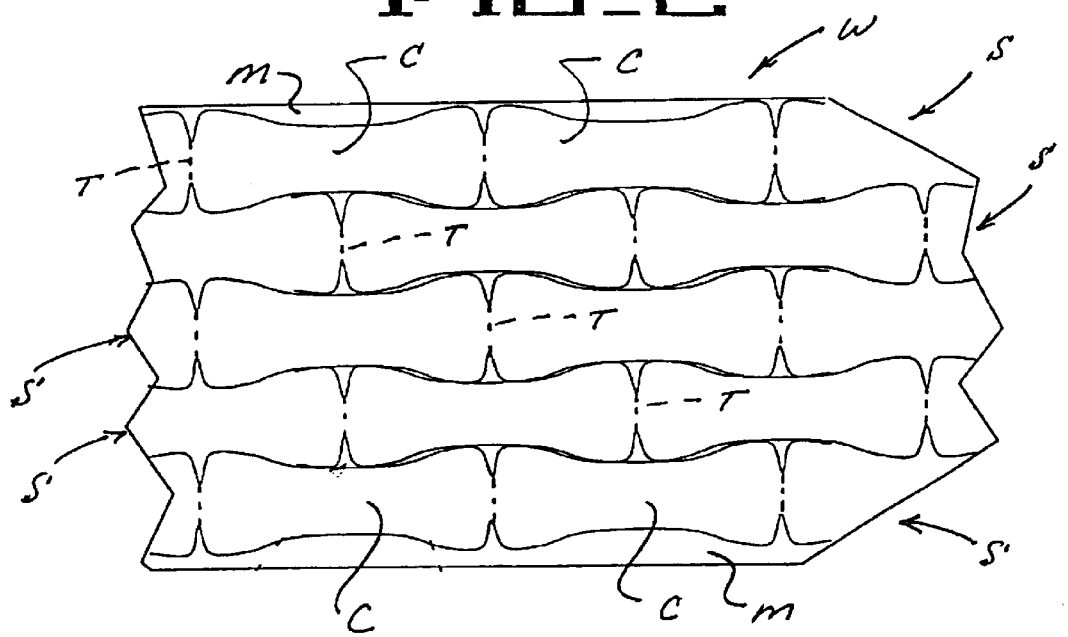
FIG_2

FIG_3
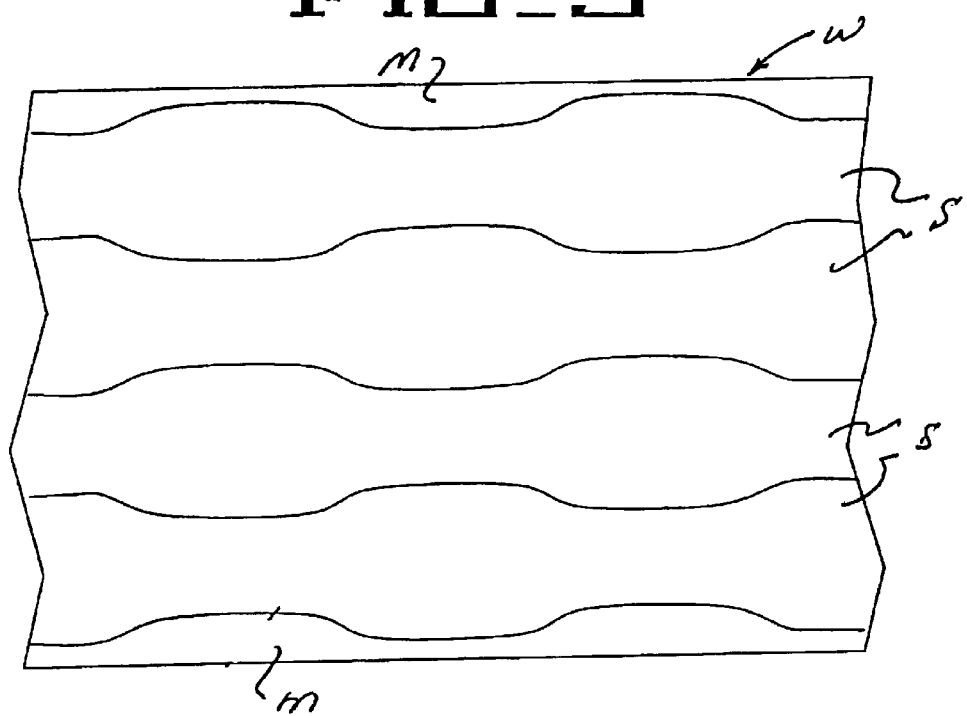
FIG_3a
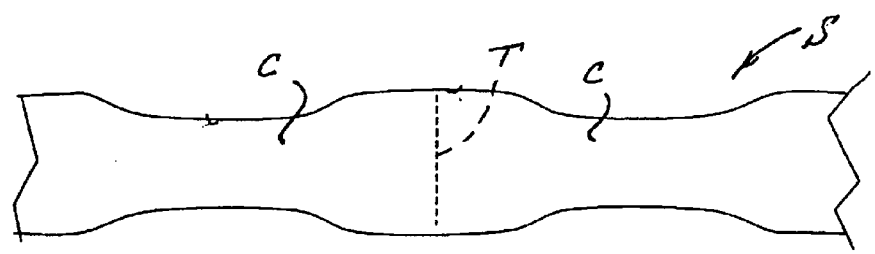
FIG_3b
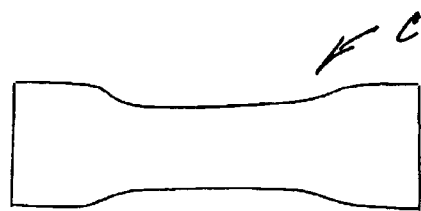

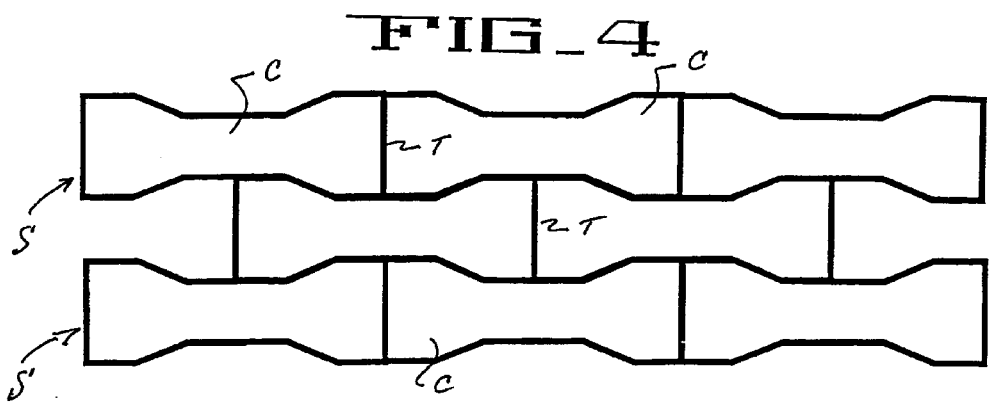
FIG_4
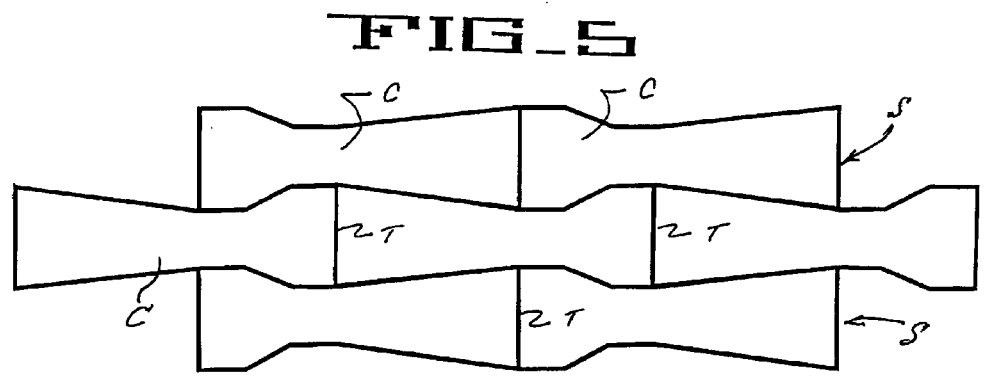
FIG_5
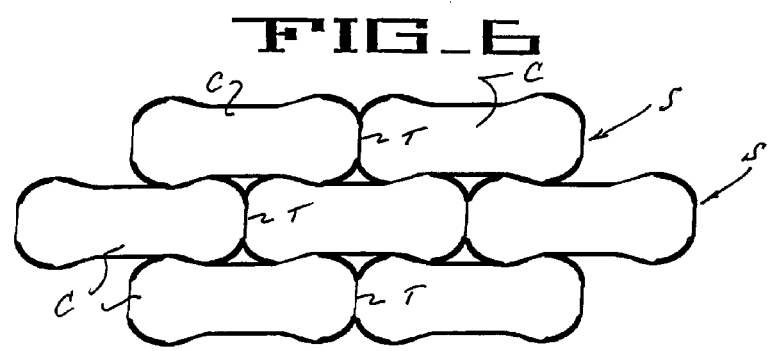
FIG_6

METHOD OF MAKING SHAPED COMPONENTS FOR DISPOSABLE ABSORBENT ARTICLES

TECHNICAL FIELD

The present invention relates generally to formation of disposable absorbent articles, such as baby diapers, sanitary napkins, adult incontinent products, disposable training pants, and the like, and more particularly to a method of making shaped components for such articles, such as absorbent cores or other absorbent components, by longitudinally slitting a relatively wide web of material into a plurality of subdivided webs, with each of the subdivided webs having a plurality of the shaped components arranged in serial relationship. Individual ones of the shaped components are formed by transverse cutting of each subdivided web.

BACKGROUND OF THE INVENTION

One of the desired performance objectives of disposable, personal care absorbent products is to provide an article that provides proper fit for the wearer, while maximizing containment with minimal leakage. It has been found that the ideal shape for absorbent components of articles such as disposable diapers, adult incontinent articles, and training pants are those which tend to be narrower in the crotch region, than in the front waist region, and rear region under the buttocks. By use of absorbent components shaped in this fashion, the desired fit and containment characteristics are maximized, while leakage is minimized. Similarly, sanitary napkins have also been found to be more comfortable when they are generally hourglass-shaped or dumbbell-shaped, with a narrower center portion, and relatively wide end portions.

In the case of disposable baby diapers and training pants, there are conflicting considerations between problems of urine leakage, and the width of the absorbent component in the crotch region of the article. For example, on a toddler, the minimum diaper absorbent core width in the crotch that allows the best fit is on the order of about 60 millimeters, depending on the specific design of the product. It has also been found that as the diaper absorbent core crotch region is made less than 95 millimeter in width, urine leakage tends to be a significant problem. There are several reasons for this. By making the core crotch very narrow, the amount of absorbent material in this region that is available to manage fluid surges becomes inadequate. There is insufficient void volume, and insufficient surface area, in order to pass the liquid into the core, and manage it in this area of heavy loading. Another mechanism by which the crotch shape of absorbent core affects leakage performance is its ability to seal against the leg of the wearer in the crotch area and in the region forwardly thereof, preventing liquid from getting off of the core surface. The body position of the wearer is highly variable, and finding the shape that gives the most consistent seal requires special consideration.

As the absorbent core of an article in the crotch region is widened, the core is required to bunch-up into a pleated shape or condition in order to fit the crotch region between the legs of the wearer when the legs are closer together than the width of the diaper crotch area. In addition to being uncomfortable, this geometrically tends to pull the diaper downwardly. Other conflicting considerations arising from use of a widened core in the crotch region is that ideally, functionally elasticized leg flaps are typically desirably placed a minimal distance from the core, such as contemplated by U.S. Pat. No. 3,860,003, to Buell. If the crotch region of the core is made wider, these leg elastics are then required to be more widely placed, which in turn causes it to be necessary to make the crotch width in the envelope or "surrounds" of the diaper wider as well, since these components must be positioned outwardly of the leg elastics. This wide envelope crotch portion, when bunched-up between the legs of the wearer, causes wrinkles that tend to gather the waist of the diaper inwardly.

The net consequence of a diaper absorbent core crotch portion being wider than ideal is threefold. The crotch of the article is perceived as bulky and uncomfortable, the diaper cannot be pulled up as far so it seems to be shorter in length, and the waist material is bunched toward the centerline of the article, so that the waist size is perceived as being smaller.

Those skilled in the art are aware of the compromise between fit and leakage performance. Because consumers tend to place a higher value on leakage performance than they do on fit, there is a tendency to have crotch regions of absorbent articles be relatively wide, much wider than the ideal. For example, most size "large" disposable baby diapers sold in the United States markets have absorbent core crotch portions between 90 millimeters and 100 millimeters wide. This is much wider than the ideal 60-70 millimeter width that would yield the best fit. In the context of the present invention, this means that it is necessary to have the ability to design an absorbent core crotch portion to the shape which is known to provide the best value.

In the front waist region of disposable diapers (and to a lesser degree in disposable training pants), it has been found to be advantageous to have a wider core, in order to minimize leakage. There are several reasons for this. It has been found to be advantageous to have the sides of the absorbent core in contact with the wearer's legs in order to quickly absorb any liquid in that region, rather than risking allowing liquid to pool there behind the leg flaps. In order to follow the shape of the front of the thighs far enough forward to be effective, an absorbent core should contact the curves of the thighs toward the front, until the core is much wider. For example, a size "large" baby diaper would ideally need to follow the thighs until it is at least 110 millimeters wide to take advantage of this sealing effect. Many designs are much wider than this.

A second reason for broadening or widening of the absorbent core in the front of the diaper is to provide sufficient surface area in order to manage fluid surges. There has been a great deal of technology developed to manage urine surges. For example, U.S. Pat. No. 5,490,846, to Ellis, discloses the application of low density nonwoven fabric structures intended to provide sufficient void volume in the core to rapidly acquire surges. U.S. Pat. No. 5,294,478, to Wanek, teaches the application of a two-layered acquisition structure, with a lower layer that is more hydrophillic and with a smaller average core size than the upper layer. However, a problem with these materials is that they are still inadequate in some situations to absorb urine sufficiently rapidly, and as a result, liquid flows downwardly on the surface of the diaper core. If the baby is laying on its side, it is a very short distance before the liquid runs off of the core. U.S. Pat. No. 4,695,278, to Lawson, contemplates the use of upstanding barrier cuffs which run laterally along the sides of the core, and are intended to stop any of this liquid runoff, and redirect it back into the core. In the front region of a diaper, the cuffs are flat against the body, and the resulting channel formed behind them and the associated barrier effect, are very unreliable. Liquid reaching the sides of the core in the front region of the diaper is likely to run off the core, and out the leg. Those skilled in the art know that a baby laying on its side, particularly a boy, presents one of the most challenging positions in terms of leakage containment. By making the absorbent core wider in the front of the diaper, and at a minimum, filling the entire region between the barrier cuffs with core material, it is possible to increase the distance that the liquid can run downwardly toward the side of the diaper, before it reaches the edge of the core. Leakage is thus reduced. Ideally, this requires an absorbent core wider in the front waist region than in the crotch region.

A third advantage to having a wider core in the front of the diaper is that it is a relatively short distance for liquid to travel out the front waist region. Many designs employ elasticized waistbands and elasticized barrier flaps along the waistband of the diaper, intended to stop run-off from leaking out the waist when the wearer is in the front position. These features have not proven to be reliable, and a wider absorbent core in the front waist region provides more absorbent material to absorb this flow.

Another advantage to having a somewhat broader absorbent core in the front region of a diaper is that the core material causes the tape landing zone (TLZ) for the closure tapes to be held in a flat, smooth condition. This makes the fastening system somewhat easier to operate. If the absorbent core is narrower than the landing zone, then a "step" in the height of the landing zone is observed at the outer edges thereof, making fasteners secured at these areas less secure.

In the case of disposable diapers, it has been found by those skilled in the art that it can be advantageous for the absorbent core to be somewhat wider in the back of the diaper, under the buttocks, as well as wider in the front. This is reflected in a majority of typical United States domestic diaper designs. Bowel movements in infants are frequently very liquid, and leakage is a significant problem. Those skilled in the art know that the back portion of the absorbent core absorbs the liquid from the BM, increasing the viscosity, and rendering it much less mobile. Any BM that contacts the core is dewatered in this manner. Any BM that falls to the sides of the core is not dewatered, and has a much greater chance of leaking out the leg. Those skilled in the art know that by making the absorbent core in the back somewhat wider, until it fills the zone between the barrier cuffs, results in BM leakage that is frequently reduced, depending on the diaper design.

In sanitary napkin applications, the design goal is for the fit to allow the napkin to conform to the body, automatically position itself on the wearer, provide an acceptable level of comfort, and provide discrete appearance. U.S. Pat. No. 3,805,790, to Kaczmarzyk, teaches that after doing anatomical studies, it was found that there was less variation in the perineal region than was originally thought. This patent teaches that the ideal narrowest width for the sanitary napkin is between 1.25 and 1.75 inches. The lateral sides of the sanitary napkin should have a radius to fit against the legs greater than 2 inches and less than 4 inches. The arch length should be between 1.25 and 5 inches along these lateral edges. In a manner similar to diaper design, there exists a trade-off between the width at the narrowest point of the napkin, and the incidence of leakage and soiling. As a consequence of these design requirements, most sanitary napkin designs in the United States have an absorbent core shape which tends to be dog bone shaped, or hourglass-shaped, and rounded on the ends. Again, the requirement is for a non-rectangular core for sanitary napkin applications.

Absorbent articles using preformed absorbent cores are known in the prior art. As will be further discussed hereinafter, the present invention relates to formation of shaped absorbent components, such as absorbent cores, for disposable absorbent articles, which are first formed on a wide-web machine, longitudinally slit into two or more individual subdivided webs, and then delivered to a converting machine, in some appropriate package, in order to be converted into the finished absorbent articles. The alternative to this formation technique is to form an absorbent core on the converting machine itself. Some examples of technologies for producing these preformed absorbent cores include air-laid, wet-laid, and carded webs. These cores may incorporate cellulosic fibers, such as wood pulp fibers or cotton linters, superabsorbent polymeric materials, and synthetic staple fibers. These cores may also incorporate cross-linked cellulosic fibers, or cellulosic fibers which have been otherwise modified chemically to enhance their properties.

There are several reasons why it is advantageous to use a preformed absorbent core structure made on a wide web machine, rather than making the core structure on the converting line. First, the degree of complexity of the converting line is desirably reduced. By moving processes such as core formation off-line, the possibility of the line going down is reduced. This is particularly advantageous in connection with manufacture of more complex product designs, where many unit operations are involved. Secondly, wide web technologies have generally proven to reduce variation in basis weights, relative to traditional core formation systems done on converting machines themselves. This reduction in basis weight variation, combined with the simplification of the converting line, ultimately facilitates operation at higher line speeds.

Another advantage of off-line manufacture is that as absorbent cores become thinner, it is necessary to introduce additional core manufacturing technologies, such as thermal bonding, resin bonding, incorporation of staple fibers, and the like, in order to optimize the performance of the absorbent cores. These technologies are more readily implemented on a wide web machine that runs continuously, rather than on individual converting machines that typically start up and shut down relatively frequently. From the consumer standpoint, the preformed absorbent cores tend to be much thinner than the conventional cores, providing the potential for significantly enhanced fit.

One problem with current practice for making preformed cores on a wide web machine is that the web is slit in straight lines, and the resultant absorbent cores are rectangular in shape. The designer of the absorbent article is then required to cut the core to the desired shape, resulting in material waste, or must compromise between narrow dimensions in the center region, and wider dimensions in the end regions of the core. In applications requiring absorption of urine, the consumer places a high value on leakage performance, and leakage performance is enhanced by having a wider core. Consequently, the core widths frequently are chosen wider than diaper designs made with conventional cores. The crotch regions are therefore typically bulky, which negates much of the perceived value of having a much thinner, preformed core. Alternatively, the converter can die-cut the preformed core material into a more fitted shape, but this can result in significant material waste.

There have been a significant number of developments in the prior art aimed at producing a fitted shape from a rectangular core, while minimizing or eliminating material waste. European Patent No. 670153 teaches cutting a rectangular web into a substantially hourglass shape, while leaving the cut-outs attached at the root of the crotch portion. The cut-outs are folded over on top of the web, resulting in higher base weight in the crotch, as well as a no-waste application. While the additional basis weight in the crotch area is sometimes desirable, the shape of this double layer region is frequently complex, and results in thicker edge portions in the crotch region. The resulting center region can then take on a lumpy appearance.

PCT Patent No. WO/9829070 teaches that a pair of webs, which are shaped and include protruding structures, are partially nested in order to reduce the waste. While saving some waste, there is still some waste present in this arrangement, and there is thus a conflict between the degree of nesting that can be achieved, and the quantity of waste that results.

U.S. Pat. Nos. 5,695,846 and 5,597,437 teach the practice of cutting a fully shaped absorbent core from a continuous web, and then superimposing the removed strips onto the core. The removed strips are attached in a manner such that the complementary shapes on the strips coincide with the shape of the fully shaped core to which they are laminated. In order to do this, the design options for the core are severely limited to shapes where the complementary strips of material removed from the sides of the web can superimpose perfectly on the shaped core from the center of the web.

U.S. Pat. No. 6,171,432 teaches the practice of slitting a rectangular web into two webs, with a single shaped cut forming two strips each with one straight side and one shaped side. They are repositioned, phased, and joined to one another along the straight side, forming a longitudinally symmetrical web with shaped sides. This method also severely limits the types of shapes which can be used, as the complementary shapes produced by the slit must be identical when re-phased and joined together in order to produce a longitudinally symmetrical core.

SUMMARY OF THE INVENTION

The present invention circumvents the above-noted difficulties by cutting a multiplicity of individual subdivided shaped webs from a wide web, and using the principle of nesting to reduce the amount of unused trim material. When used in conjunction with an air-laid process that does not use materials incompatible with continuous recycle through the process, any trim that is produced can be recycled into the process, desirably resulting in no material waste. The use of the most efficient nesting pattern is encouraged, since recycled materials is subtracted from the throughput of the machine. Any repeating shape design which is intended to be fed into a converting machine can be done, with the subdivided webs cut transversely into identical cores.

In accordance with the present invention, a method of making shaped components, such as absorbent cores, for disposable articles, comprises the steps of providing a web of material from which the components are formed. The web of material is longitudinally slit into a plurality of adjacent, subdivided webs, each having a plurality of the shaped components arranged in serial (i.e., end-to-end, or side-by-side) relationship. Each of the shaped components has a non-rectilinear configuration, that is, is non-rectangular and having non-linear side edges.

Individual ones of the shaped components are formed by transversely cutting each of the subdivided webs. It is contemplated that the shaped components can be provided in roll form to a converting machine, with transverse cutting of the shaped components effected in conjunction with absorbent article manufacture. Alternatively, it is contemplated that a carrier web can be provided, with the transversely cut, individual shaped components placed on the carrier web. The carrier web can then be employed in conjunction with absorbent article manufacture. For some applications, it can be desirable to stack individual ones of the shaped components after they are transversely cut from the subdivided webs. Depending upon the exact configuration of the shaped cores being formed, non-linear cuts can be transversely formed in the subdivided webs.

In accordance with the preferred practice of the present invention, the shaped components of adjacent ones of the subdivided webs are nested with each other, that is, a line running longitudinally of the wide web of material extends through the shaped components of adjacent ones of the subdivided webs. This preferred practice of the present invention desirably acts to minimize waste from the wide web of material as the subdivided webs of shaped components are formed. The present method further contemplates that for some applications, opposite marginal portions of the wide web of material are collected, that is, those portions respectively positioned outwardly of outboard ones of the subdivided webs. The collected marginal portions are at least partially recycled, thus further desirably limiting waste which is formed attendant to shaped component manufacture.

As discussed hereinabove, specific configurations of shaped components for disposable absorbent articles provide such articles with the desired fit and performance characteristics. To this end, each of the shaped components has at least one end portion having a transverse dimension greater than a transverse dimension of an intermediate portion thereof, such as for formation of dog bone-shaped or hourglass shaped absorbent cores, or other shaped components.

The configuration of the shaped components of the subdivided webs is selected to further facilitate efficient use of the wide web of material from which they are formed. Waste material from between adjacent ones of the subdivided webs is minimized by juxtaposition of adjacent ones of the subdivided webs, with the subdivided webs being complementary with each other. In one illustrated embodiment, adjacent ones of the subdivided webs have reversely-oriented, repeating patterns of the shaped components. In accordance with the illustrated embodiments, the shaped components of adjacent ones of the subdivided webs are staggered. While the shaped components shown in the illustrated embodiments are identically shaped in each respective embodiment, it will be appreciated that the shaped components may be non-identical, i.e., shaped differently from other ones of the components.

Depending upon the end use of the shaped components formed in accordance with the present invention, the components may be formed from a wide variety of materials, including cellulosic fibers, typically wood pulp fibers, as well as synthetic fibers. Shaped components comprising non-fibrous materials, such as plastic films, can also be formed in accordance with the present invention. For formation of shaped components for use as absorbent cores in disposable absorbent products, the wide web of material from which the components are formed preferably comprises wood pulp fibers, and may optionally include superabsorbent polymeric material.

Other features and advantages of the present invention will become readily apparent from the following detailed description, the accompanying drawings, and the appended claims.

BRIEF DESCRIPTION OF THE DRAWINGS

FIG. 1 is a diagrammatic view of a system for forming shaped components for disposable absorbent products illustrated as an air-laid formation apparatus with waste recycling, embodying the principles of the present invention;

FIG. 2 is a diagrammatic view of a web of material slit longitudinally in accordance with the present method to form a plurality of subdivided webs having shaped components;

FIG. 3 is a view similar to FIG. 2 diagrammatically illustrating a longitudinally slit web having a plurality of subdivided webs;

FIG. 3a is a diagrammatic view of one of the subdivided webs shown in FIG. 3, showing shaped components thereof;

FIG. 3b is one of the shaped components formed from the subdivided web of FIG. 3a, illustrated as a shaped diaper absorbent core;

FIG. 4 is a diagrammatic view of shaped components of adjacent subdivided webs formed in accordance with the present invention, wherein a fully nested, complementary diaper absorbent core design is illustrated, which design is symmetrical along a transverse axis thereof;

FIG. 5 is a diagrammatic view of shaped components of adjacent subdivided webs formed in accordance with the present invention, wherein fully nested, complementary absorbent cores are illustrated, the design of which is asymmetrical along a transverse axis, showing adjacent subdivided webs having reversely-oriented, repeating patterns, with adjacent subdivided webs requiring reversed winding; and FIG. 6 is a diagrammatic view of shaped components of adjacent subdivided webs, with the shaped components configured as a non-complementary sanitary napkin design which results in some trim recyclable material being formed between adjacent, subdivided webs.

DETAILED DESCRIPTION

While the present invention is susceptible of embodiment in various forms, there is shown in the drawings, and will hereinafter be described, a presently preferred embodiment, with the understanding that the present disclosure is to be considered as an exemplification of the invention, and is not intended to limit the invention to the specific embodiments illustrated.

The present invention relates to formation of shaped components for disposable absorbent articles, which components may be provided in the form of absorbent cores, liquid transfer layers, or other components of disposable absorbent articles. While the present disclosure presently contemplates air-laid formation of a wide web of material from which a plurality of subdivided webs are formed, each having a serial arrangement of shaped components, it will be understood that the principles disclosed herein can be employed for formation of shaped components from a web of material which is formed other than by air-laying.

Air-laid technology is one of the more predominant technologies for use in preformed absorbent core manufacture. So-called air-laid is a nonwoven material composed of an assembly of fibers or filaments held together in a random sheet by mechanical interlocking through fusing or bonding. Nonwoven materials are generally classified by the fibers used, and the manner in which the web is formed or bonded. The prices of nonwoven materials differ depending upon the materials from which they are formed. Nonwoven materials made from synthetic fibers typically command higher prices than nonwoven materials made from natural materials.

Air-laid is used primarily in absorbent products, and offer properties typically not provided by conventional wet-laid paper or synthetic nonwoven materials. These properties include cloth-like feel, softness and superior bulk and strength, combined with absorbency. Recent advances in the production of air-laid include the ability to inject superabsorbent polymeric materials, and superabsorbent and/or bi-component fibers into the material, creating fabrics with higher levels of absorbency. The improved performance characteristics of these materials permit products to be redesigned, and new end-use products to be developed.

Air-laid is produced from a suspension of cellulose fibers in air. Commercial air-laid production did not begin until the 1970's. The aid-laid process begins with hammer mills that breakdown cellulosic fibers into component fibers. Pressurized air suspends the fibers, and distributes them through one or more forming heads to create a web on a moving forming wire (i.e., screen). The web is then bonded, and the fabric is dried in ovens. A calendering process, which determines the density of the finished fabric, compresses the fabric. Synthetic bonding fibers, absorbent powders, and other fillers may be added before, within, or between the forming heads used in the process. The addition of these materials imparts specific properties to the finish fabric. By varying the fiber type, fiber length, additives, and speed of the moving forming wire, a variety of air-laid fabrics with different absorbent qualities, thickness, and strength, among other characteristics, can be produced. Existing technology permits commercial production of air-laid fabrics with basis weights from 40–2000 grams per square meter. Air-laid production offers advantages over the traditional wet-laid method due to its negligible need for water, greater production flexibility, lower capital costs, and higher selling prices.

Latex and thermal bonding methods are generally used to bond the air-laid web. Latex bonding uses a liquid latex binder that is sprayed onto the form web, which is then cured in an oven. Latex bonded fabrics have a cloth-like look and feel, and may be used in place of conventional tissue, cloth, and synthetic woven fabrics.

Thermal bonding involves the addition of synthetic wood pulp (polyethylene fiber which melts in the hot air oven forming bonds with adjacent fibers) or bi-component fibers to the web, which is then subjected to high temperatures to fuse the fibers to other components in the web. A modified thermal bond air-laid process produced multi-bond fabrics, with the addition of a small percentage of latex binder. In general, thermal and multi-bonded fabrics offer superior absorbency and softness, compared to latex bonded fabrics, and are suitable for use in redesigned and newly developed personal hygiene products which require ultra-thin, fast wicking, absorbent cores.

After the air-laid web has been bonded, it is trimmed to size, wound into large parent rolls, and custom slit in widths to meet the converter requirements. During this process, some portion of the parent rolls is lost as waste (in the form of off-grade, culled slit rolls and edge trim). The slit rolls are shipped to the manufacturer who will then convert them into end-use products, which are in turn packaged and distributed.

A clear drawback in the typical air-laid production operation is the need to efficiently handle or reuse what is now considered waste. The waste products that are formed at start-up, as off-specification product, or edge trim from converting operations, are on-going, and costly. It is important to address issues concerning efficient recycling of the waste. Ultimately, waste is typically sold in a secondary use market, or sent to a landfill. In either case, waste is a large financial burden and loss for an air-laid operation. It is difficult to recycle these waste materials back into the forming process because they contain components (such as latex binders and melted synthetic fibers) that negatively impact the performance of the end product, and are difficult to separate into their individual components for reuse.

Another weakness of the current typical air-laid, preformed core process is that straight (linear) slitters are used. These produce web materials that ordinarily are used to produce rectangularly shaped absorbent cores, which as discussed above, are not optimized for fit.

In accordance with the present invention, trimmed opposite marginal portions of the wide web of material used in the process are removed from the moving web, such as via vacuum hoses, and are transported through ducts which carry them to the defiberizing mill to be recycled into the process. Typical air-laid webs contain materials that have proven to be incompatible with long-term recycling in the existing hammer mill designs. Under heat and friction, many materials present in the air-laid sheet, such as latexes and polyethylene, will cause build-up of material on the internal surfaces of the mill. This build-up also tends to incorporate paper fibers and forms hard, brittle masses. These tend to break loose after they reach a certain size, and are deposited in the web being formed. They can be easily seen and felt, and in their least desirable form, can have very sharp edges. For example, on a typical swinging hammer-type mill, the square ends of the hammer are one area on which build-up occurs, particularly in the leading corner of the hammer. When these pieces break off, they resemble a toothpick, with a sharp hook on one end, and thus constitute a very undesirable type of contamination to have incorporated in an absorbent core. These problems have prevented the routine practice of recycling material through the hammer mill. By eliminating such incompatibility, material can be recycled as the normal part of the manufacturing process, and the advantages associated with that recycling can be realized.

There are several methods that can be utilized to circumvent the problems associated with recycling. One method is to redesign the mill so that the temperatures and conditions which result in build-up are not present. The mill can be redesigned to be made easier to clean, and then cleaned periodically. Use of secondary mills or buster blowers, which can break-up the recycled material into individual fibers, and allow recycling to take place without going through the primary mill itself, is also a method which can be applied.

The most desirable method for avoiding recycling problems is to simply remove those materials from the air-laid formulation which cause the build-up to take place. The preferred absorbent material, ordinarily wood pulp fluff optionally including superabsorbent polymeric material, is particularly well suited for use as absorbent cores in disposable absorbent articles such as diapers, feminine hygiene products, incontinence devices, and the like. This material is easily recycled without causing build-up problems, and without appearing as visually discernible pieces of recycled material in the final air-laid web. In the preferred form, a blend or mixture of cellulosic fibers and superabsorbent polymeric material disposed in and amongst the fibers of the pulp is employed. This preferred practice provides an absorbent material containing cellulosic fibers and superabsorbent polymers (SAP) which material is soft, thin, and of high density. Additionally, the material has enhanced absorption properties (absorption rate and wicking), and firmly entraps the superabsorbent polymer in the fiber network without the use of any chemicals or binder. The absorbent structure has enough integrity (i.e., strength) to be processed on conventional disposable product manufacturing equipment without web breakage.

In one aspect of the present invention, an absorbent material is provided that contains from about 40 weight percent to about 90 weight percent cellulosic fibers, and from about 10 weight percent to about 60 weight percent superabsorbent polymeric material. The material has a water content of less than about 10 weight percent. As used herein, the phrase "weight percent" means weight of substance per weight of final material. By way of example, a 10 weight percent SAP means 10 grams per square meter SAP per 100 grams per square meter basis weight of the material.

Cellulosic fibers that can be used in the material of the present invention are well-known in the art, and include wood pulp, flax, and peat moss. Wood pulp fibers are presently preferred. Pulps can be obtained from various processes, including mechanical, chemical/mechanical, sulfite, kraft, pulping of reject materials, organic solvent pulping, etc. Both soft wood and hard wood species are useful, while soft wood pulps are preferred. It is not necessary to treat the cellulosic fibers with chemical debonding agents, cross-linking agents and the like for use in practicing the present invention.

Non-cellulosic fibers can also be used in practicing the present invention, as long as such fibers are of a sufficiently high melting point such that they are compatible with and can be sent through a defiberizing mill without causing build-up, or causing too much degradation of the properties of those fibers.

An absorbent material for practicing the present invention can contain any superabsorbent polymer material, which are well-known in the art. As used herein, the term "SAP" means a substantially water-insoluble polymeric material capable of absorbing large quantities of liquid in relation to its weight. The superabsorbent polymer can be in the form of particle material, flakes, fibers, and the like. Exemplary particulate forms include granules, pulverized particles, spheres, aggregates, and agglomerates. Exemplary and preferred superabsorbent polymers include salts of cross-linked polyacrylic acid such as sodium polyacrylate. Superabsorbent materials are commercially available, such as from Stockhausen GmbH, Krefeld, Germany.

In accordance with the preferred practice of the present invention, the material from which the relatively wide web is formed comprises from about 50 to about 90 weight percent cellulosic fibers, more preferably from about 60 to 80 weight percent cellulosic fibers. The web of material preferably comprises from about 10 to about 50 weight percent superabsorbent polymeric material, and more preferably from about 20 to 40 weight percent superabsorbent polymer.

A web of absorbent material for practicing the present invention is made by using an air-laying system which can be configured in accordance with known technology. In accordance with the present system 10 illustrated in FIG. 1, cellulosic fibers (e.g., wood pulp fibers) are processed using a hammer mill 12 to individualize the fibers. The individualized fibers can be blended with superabsorbent polymer granules in a suitable blending system, and pneumatically conveyed into one or more forming heads 14. As is known in the art, the blending and distribution of absorbent materials can be controlled separately for each of the forming heads 14. Controlled air circulation and winged agitators in each chamber produced a uniform mixture and distribution of wood pulp and superabsorbent polymer. The superabsorbent polymer can be thoroughly and homogeneously blended throughout the web W being formed, or contained only in specific strata by distributing it to selected ones of the forming heads.

Wood pulp fibers (and optionally superabsorbent polymer) from each forming chamber are deposited by vacuum onto a forming wire or screen 16, which is typically covered with tissue paper T to reduce the loss of material. The tissue paper can be removed prior to calendering of the web W, or can be incorporated into the formed web of material.

An absorbent material which is preferred for practice of the present invention is of a high density, and has a density greater than 0.25 grams/cc. In preferred embodiments, the material has a density in the range from about 0.30 grams/cc to about 0.50 grams/cc, more preferably from about 0.30 grams/cc to about 0.45 grams/cc, and most preferably from about 0.35 grams/cc to about 0.40 grams/cc.

Air-laid absorbent structures are typically produced with a low density. To achieve higher density levels, such as preferred for the web of material for practicing the present invention, the air-laid material is compacted using compaction or calender rolls 18 as shown in FIG. 1. Compaction is accomplished using techniques as are well-known in the art. Typically, such compaction is carried out at the temperature of about 100° C., and at a load of about 130 newtons per millimeter. The upper compaction or calender roll is typically made of steel, while the lower roll is a flex-roll having a hardness of about 85 SA D. It is preferred that both upper and lower compaction rolls be smooth, although they can be embossed as is known.

In accordance with the present method of making shaped components, such as shaped absorbent cores for disposable articles, the apparatus such as illustrated in FIG. 1 is employed to provide a web of material from which the components are formed. In accordance with the present invention, a slitter 20 is provided for longitudinally slitting the web of material into a plurality of adjacent subdivided webs S (see FIG. 2). Each of the subdivided webs S has a plurality of shaped components C arranged in serial relationship, that is, either arranged end-to-end, as illustrated, or side-by-side, as may be desired for some applications.

The subdivided webs S are preferably slit and formed simultaneously (i.e., in parallel) rather than by serial slitting on individual machines, desirably reducing machine complexity. While formation of substantially identical slits in the web W can be suitable for some forms of practicing the present invention, non-identical slits may be suitable for other applications, including formation of non-identical shaped components C which are configured for efficient nesting.

In accordance with the present invention, the shaped components each having non-rectilinear configuration, that is, they are non-rectangular in shape, and have contoured non-linear side margins, and linear or non-linear end margins.

The system 10 illustrated in FIG. 1 for practicing the present invention has been specifically configured to facilitate efficient formation of the present shaped components, in that the system is configured for collection of opposite marginal portions M of the web of material which has been air-laid. These marginal portions M, respectively positioned outwardly of the outboard ones of the subdivided webs S, are collected and at least partially recycled in the system. Collection is effected by way of pneumatic conveyor 22 which conveys the collected marginal portions M from the region at the slitter 20 at which the web W is cut, and returns the marginal portions M to the hammer mill 12 for recycling. As will be appreciated, this illustrated arrangement not only facilitates efficient formation of the shaped components C, but desirably minimizes waste which is formed by effecting recycling of at least the marginal portions. Depending upon the exact configuration of the shaped components C, and the subdivided webs S, waste material may also be generated from between the webs S, which waste material may also be collected and at least partially recycled.

In the configuration of the shaped components C illustrated in FIG. 2, the shaped components of adjacent ones of the subdivided webs S are nested with each other, that is, a line extending longitudinally of web W passes through the shaped components C of adjacent ones of the subdivided webs S. In this illustrated embodiment, as in other embodiments illustrated herein, each of the shaped components has at least one end portion having a transverse dimension greater than a transverse dimension of an intermediate portion thereof. In the embodiment illustrated in FIG. 2, wherein the shaped components C are illustrated as sanitary napkin absorbent cores, it will be observed that the adjacent subdivided webs are non-complementary, that is, there are portions of the web of material W between adjacent ones of the subdivided webs S which are cut from the web, and do not form parts of the shaped components being formed. Such material is kept to a minimum by virtue of the nested configuration of the shaped components. In other embodiments disclosed herein, adjacent ones of the subdivided webs S are complementary and juxtaposed, thus avoiding the creation of waste material between adjacent ones of the subdivided webs.

Each of the subdivided webs S is cut transversely, as indicated in phantom line at T, to form individual ones of the shaped components C. As will be appreciated, shaped components C arranged serially in side-by-side relationship which are separated by cutting transversely of the subdivided webs S will have such cuts extend longitudinally of the components being formed. For some applications, it can be desirable to form individual ones of the shaped components immediately after the web W is longitudinally slit into subdivided webs. For such applications, it can be desirable to provide a carrier web, with individual ones of the shaped components placed on the carrier web for subsequent storage and shipment in roll form, and ultimate use by a converter for absorbent product manufacture.

Alternatively, individual ones of the shaped components can be stacked for ultimate use by the converter. In one form, the shaped components can be stacked as if they comprise the bound pages of a book. Suitable adhesive material or tape can be provided to act as a "book binding" for such a stacked array, allowing it to be restrained as the associated converting machine removes the individual shaped components, i.e., the "pages" of the book. The "pages", i.e., the shaped components, can each be attached in this fashion at an expansive surface, rather than at edge portions thereof. A machine can be easily constructed to pull individual components off of the stacked array, with the components naturally in registration without any feedback devices.

In another form of practice of the present invention, each subdivided web can be stored in roll form, without transverse cutting of the webs to form individual ones of the shaped components. The rolled, subdivided webs are then provided to a converter, who effects the transverse cutting of the webs, and use of the individual shaped components thus formed for absorbent product manufacture.

The subdivided webs can also be provided in the form of spooled rolls in order to increase the run time of the roll, or also festooned in boxes. In one form, festooning can be effected so that a subdivided one of the webs of serially arranged shaped components is folded back-and-forth on itself, with creases formed so that they correspond with the transverse cuts to be formed between adjacent ones of the components. Such festooning or folding can be effected at every component, every other component, etc. The crease formed by festooning in this fashion does not need to be located at the region of the transverse cuts between adjacent shaped components, but it is preferred to keep the festoon crease out of the middle portion of each shaped component. In-phase festooning can be enhanced by pre-creasing the subdivided web. Pre-creasing is preferably effected in close proximity to the cutting apparatus which forms shaped components. A machine can easily be constructed that pulls a registered festooned core out of a box, in registration with the machine, by grasping the crease, thus avoiding the need for any other registration controls.

Another arrangement by which subdivided webs can be handled is through the use of an apparatus having a feed mechanism including a wheel or drum, or like component, having a peripheral surface formed corresponding to the outline of a subdivided web of the shaped components. By machining the outline of a series of shaped components on a feed drum or the like, with the surface of the drum having a deep recess with tapered sides, and with the repeating component outlines fitting perfectly into the feed drum, registration of the components is effected, with efficient tracking of the subdivided web. In such an arrangement, precise tracking and registration can be facilitated by a severe narrowing of the subdivided web at each location where a transverse cut is to be formed between adjacent ones of the shaped components. Such an arrangement provides the strongest mechanical registration forces with a feed roller drum having this machined surface configuration. Such narrowing of the subdivided web also facilitates transverse cutting to form the individualized shaped components, and extends the maintenance cycle of the cutting equipment. In a variation of the above-described arrangement, a hole can be punched in the subdivided web at each point where a transverse cut is to be formed, with suitable teeth on a feed drum for the web engaging these holes, thereby drawings the web forward in phase with the associated converting apparatus.

While the illustrated embodiment shows the transverse cuts T as being generally linear, it will be understood that it is within the purview of the present invention that non-linear transverse cuts can be formed in each of the subdivided webs S for formation of shaped components C.

Shaped components in the form of absorbent cores formed in accordance with the present invention will now be described in relationship to their use in specific disposable articles. For purposes of the present invention, disposable absorbent articles are articles which absorb and contain liquid such as body exudates, and are intended to be discarded after a limited period of use.

Disposable absorbent articles, such as diapers, feminine hygiene products, adult incontinence devices, and the like, have found widespread acceptance. To function efficiently, such absorbent articles must quickly absorb body fluids, distribute those liquids within and throughout the absorbent article, and be capable of retaining those body liquids when placed under loads. In addition, absorbent articles need to be sufficiently soft and flexible so as to comfortably conform to body surfaces.

While the design of individual absorbent articles varies depending upon use, there are certain elements or components common to such articles. Disposable absorbent articles typically include a liquid pervious top sheet or facing layer, which facing layer is designed to be in contact with the body surface. The facing layer is made of material that allows for substantially unimpeded transfer of fluid from the body into the absorbent core of the article. The facing layer should not absorb fluid, per se, and thus should remain dry. An absorbent article typically further includes a liquid impervious back sheet or backing layer disposed on the outer surface of the article, which layer is designed to prevent the leakage of liquid out of the article.

Disposed between the facing layer and backing layer is an absorbent member referred to in the art as an absorbent core. The function of the absorbent core is to absorb and retain body liquids entering the absorbent article through the facing layer. Because the origin of body liquids is localized, it is necessary to provide the means for distributing fluid throughout the dimensions of the absorbent core. This is typically accomplished either by providing a distribution member disposed between the facing layer and absorbent core and/or altering the composition of the absorbent core, per se.

Liquid can be distributed to different portions of the absorbent core by means of a so-called transfer or acquisition layer disposed between the facing layer and the core. Because of the proximity of such an acquisition layer to the body surface of the wearer, the acquisition layer should not be formed from material that retains large amounts of liquid. The purpose of the acquisition layer is to provide for rapid transfer and distribution of liquid to the absorbent core.

As discussed above, the absorbent core is typically formulated of a cellulosic wood pulp fiber matrix, which pulp is capable of absorbing large quantities of liquid. Absorbent cores can be designed in a variety of configurations to enhance fluid absorption and retention properties. By way of example, the liquid retention characteristics of absorbent cores can be greatly enhanced by the provision of superabsorbent polymer material integrated into the fibers of wood pulp. Superabsorbent materials are well-known in the art as substantially water-insoluble, absorbent polymeric compositions that are capable of absorbing large amounts of liquid in relation to their weight, and forming hydrogens upon such absorption. Absorbent articles containing blends or mixtures of pulp and superabsorbents are known in the art, and have been found to be particularly suitable for use in disposable absorbent articles.

The distribution of superabsorbent polymer within an absorbent core can be uniform or non-uniform. By way of example, that portion of the absorbent core proximate to the backing layer (i.e., farthest away from the wearer) can be formulated to contain higher levels of superabsorbent polymer than those portions of the core proximate the facing or acquisition layers. By way of further example, that portion of the core closest to the site of liquid entry (e.g., the acquisition zone) can be formulated to wick fluid into surrounding portions of the absorbent core (e.g., the storage zone). Ideally, the absorbent core is shaped with a narrower crotch region, and wider end regions in order to improve the fit, comfort, and appearance, as well as maximizing the absorbent performance of the product.

In accordance with the present invention, conventional straight web slitters in the wide-web process are replaced with shaped die cutters or slitters 20 for forming shaped components C. Die cutting equipment such as this is well-known in the art, and can be used to cut the wide web W into repeating shapes representing the shape of the component (e.g., absorbent core) with optimized fit. The shapes represent the completed cores attached in end-to-end, serial relationship in the illustrated embodiments. When run on the converting machine, a transverse cutter for formation of transverse cuts T is registered to the absorbent core, cutting the subdivided webs S in the correct location to produce repeating, identical cores of the preferred shape. This can be accomplished using automatic registration equipment that looks for a structure or a mark on each core, and phases the cutting knife in relationship to that mark.

Inherent in most any system designed to cut multiple shaped components from a wide web is the presence of some waste. In order to recycle this waste material in an air-laid process, such as illustrated, it is transported back to the hammer mill where it is defiberized and fed back into the process along with virgin wood pulp fibers.

Even through these waste materials, such as marginal portions M, are saved when they are recycled, recycling in this manner is not without its impact on the economics of the overall process. Since material that is being recycled is not being shipped, the throughput of the system is reduced by the amount that is recycled. Therefore, it makes economic sense to minimize the amount of material that goes through the recycle system. As will be appreciated, this is accomplished in the present invention by practicing various degrees of nesting of the shaped components of adjacent ones of the subdivided webs S.

With further reference to FIG. 2, and reference to FIGS. 3, 3a, 3b and 4–6, it will be appreciated that in its most effective form, nesting involves making the fitted core design symmetrical in both the machine-direction and cross-direction, that is, symmetrical about both the transverse and longitudinal axes of each shaped component C. Adjacent shaped components C in the web W are 180° out-of-phase with one another (i.e., are staggered) where the broad portion of one component is nested in the narrow portion of adjacent components. When the shapes are selected to be perfectly complementary (i.e., juxtaposed and fit together with no waste therebetween), the only waste which is generated from the web W is along the opposite marginal portions M, where the outboard subdivided webs S are adjacent to the straight parallel sides of the wide web W. Such arrangements are illustrated diagrammatically in FIGS. 3 and 4. In FIG. 3, shaped components C are being formed in a configuration to facilitate use as absorbent cores for disposable diapers. The wide web W is subdivided into a plurality of adjacent subdivided webs S, with FIG. 3a illustrating one of the subdivided webs S cut transversely at T to form shaped components C, one of which is illustrated in FIG. 3b. Marginal portions M of the wide web W constitute the only waste material generated from the wide web. FIG. 4 illustrates a similar configuration of shaped components C being formed.

While this form of complementary, juxtaposed subdivided webs for formation of shaped components is appropriate for use in some forms of product, a need exists for some products for asymmetry in the machine direction (i.e., asymmetry with respect to a transverse axis of each shaped component) in order to achieve a better approximation of the component shaped which yields the ideal fit of a disposable absorbent article. This is particularly true in connection with disposable diapers, where the narrowest part of the crotch region is preferably positioned forwardly of the transverse centerline, making the ideal shape asymmetrical in the machine direction. Fully complementary, juxtaposed shaped components can be designed incorporating asymmetry in the lengthwise direction by orienting adjacent ones of the subdivided webs in the "opposite" direction, that is, configuring adjacent ones of the subdivided webs to have reversely oriented, repeating patterns of shaped components. Such as arrangement is illustrated in FIG. 5, wherein the shaped components C of the subdivided webs S are alternatingly arranged in reversely-oriented, repeating patterns.

In such an arrangement, all of the shaped components become identically oriented when either the odd or even numbered subdivided webs S are rewound in an opposite direction, so that the orientation of the shaped components is reversed. In this arrangement, it will again be appreciated that adjacent ones of the subdivided webs S are juxtaposed and complementary, with recyclable waste material thus minimized to include only side marginal portions of the wide web. This arrangement can be the optimal configuration for some types of absorbent core designs. For some designs, such as illustrated in FIGS. 2 and 6, a third configuration is most advantageous. Rather than fully complementary shapes, the shaped components C are nested, but the adjacent subdivided webs are non-complementary. A narrow strip of material is taken from between each of the subdivided webs and collected for recycling, in addition to the opposite marginal portions of the web W. As in the other embodiments, the shaped components C are staggered, with the nested configuration minimizing material between them for recycling.

The percentage of recyclable material can be easily calculated by comparing the area of the shaped components (e.g., shaped absorbent cores) on a section of the web, to the area of the section of the web. The easiest section to calculate this against is a section of the length of one core.

$$\text{Recycle} = (WL - NA)/WL \times 100\%$$

where:
A=area of each core;
W=width of wide web;
N=number of cores that fit across the web; and
L=length of one core.

This equation is applicable to all of the situations identified above.

EXAMPLES

Example 1

This example of the present system concerns formation of an absorbent core for a disposable diaper. The core is 90 mm in the narrowest portion of the crotch, with a core length of 400 mm. The widest portion of the core is 110 mm. The core is symmetrical longitudinally and about a transverse centerline running across the midpoint of the core. The pattern is a fully complementary, hourglass shape, such as illustrated in FIG. 4, thus allowing the adjacent subdivided webs to be juxtaposed, without material removed from therebetween. The core consists of air-laid material having a basis weight of 500 grams per square meter, with 55% superabsorbent polymer by weight. The balance of the air-laid consists, by weight, of cellulosic fibers in the form of defiberized wood pulp, or carrier tissue. The density of the air-laid web is 0.35 grams per cc. The air-laid web W is 915 mm wide. The nested pattern allows the web W to be slit into nine subdivided webs S. The marginal edge trim for any fully complementary, nested shape, with the above parameters, results in a total recycle of 2.8%.

Example 2

This example also contemplates formation of shaped components for use as an absorbent core for a disposable diaper. The absorbent core has dimensions similar to those disclosed above in connection with Example 1, with a crotch width of 90 mm, a maximum width of 110 mm, and a core length of 400 mm. The pattern is symmetrical about a longitudinal centerline of each component, with adjacent subdivided webs being fully complementary. However, generally as illustrated in FIG. 5, this shaped component configuration is asymmetrical about the transverse centerline of each component. This results from the narrowest portion of the crotch region of each core being positioned forwardly of a transverse centerline of each core, with the slope of the rear core ear portions being flatter than that of the front core ear portions. The core consists of an air-laid material having a basis weight of 500 grams per square meter, with 55%, by weight, of superabsorbent polymer. The balance of the air-laid material is cellulosic fibers in the form of defiberized wood pulp or carrier tissue. The density of the web is 0.35 grams per cc. The air-laid web is 315 mm wide. The nested, fully complementary pattern allows the web to be slit into nine subdivided webs. The edge strip results in a total recycle of 2.8%. Every other subdivided web has the front of the shaped core oriented in the reverse direction. As a consequence, out of the nine subdivided webs obtained from the sheet, four of them have to be rewound in order to be oriented in the same direction as the others.

Example 3

This example concerns formation of absorbent cores for sanitary napkins employing the present system. Each core is 215 mm long, with a minimum width of 65 mm near the mid-point, and a maximum width of 80 mm near the ends. The ends are rounded on the four corners with a 30 mm radius. The cores are attached to one another longitudinally with a narrow 20 mm neck, which is intended to be cut relatively precisely with the transverse cutting blade for formation of cuts T (see FIG. 6). The air-laid web is 915 mm wide. The cores are nested (but adjacent subdivided webs are non-complementary) so that 12 subdivided webs can be obtained. With a surface area of 189.57 square centimeters per core, the resulting recycle is 9.6% of the wide web from which the shaped components are formed.

In a system where a transverse knife cut is to be formed, the shaped pattern of the shaped components may neck inwardly at the ends, thus becoming very narrow at the point where the knife cuts are made. This not only facilitates cutting, but also desirably acts to serve to make the end of the product approximately rounded.

While the present disclosure contemplates recycling of marginal portions M, as well as other waste material, back to hammer mill 12, it is within the purview of the present invention that the recycled material first be directed to a buster blower, and then recycled into the deposition chute for direction to the forming heads of the system. This avoids regrinding, but still acts to "burst" the web material into individual fibers while being somewhat less damaging to the fibers and superabsorbent polymer (to the extent that such damage exists). While it is desirable to effect 100% recycling of waste material, it is within the purview of the present invention that only a portion of the waste material be recycled, in the event that the waste material contains materials which are incompatible with recycling.

Thus, the present invention facilitates efficient formation of absorbent cores or other shaped components for disposable absorbent products which minimizes waste, while desirably configuring the shaped components for optimized performance. As will be appreciated by those skilled in the art, the present invention can be readily practiced for formation of disposable absorbent articles including diapers, training pants, feminine hygiene products, adult incontinent products, nursing pads, baby bibs, disposable changing pads, disposable burp cloths, and shaped wipes, as well as other articles which can be advantageously employed in accordance with the principles discloses herein. As will be appreciated, shaped components formed in accordance with the present invention can be formed as laminates which constitute part of the disposable absorbent article to be formed.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover, by the appended claims, all such modifications as fall within the scope of the claims.

What is claimed is:

1. A method of making shaped components for disposable absorbent articles, comprising the steps of:

forming a web by air-laying fibrous material from which said components are formed, said web formed of fibrous material selected from the group consisting of: (1) cellulosic fibrous material; and (2) a blend of cellulosic fibrous material and superabsorbent polymer;

longitudinally slitting said web of material into a plurality of adjacent subdivided webs, each of said subdivided webs having a plurality of said shaped components arranged in serial relationship each of said shaped components having a non-rectilinear configuration, said shaped components of adjacent ones of said subdivided webs being in nested relationship with each other;

collecting opposite marginal portions of said web of material, respectively positioned outwardly of outboard ones of said subdivided web, and at least partially recycling the marginal portion for formation of said web of said fibrous material;

transversely cutting each of said subdivided webs to form individual ones of said shaped components; and assembling said individual ones of said shaped components by one of: (1) stacking said individual ones of said shaped components; and (2) placement of said individual ones of said components on a carrier web for subsequent storage and shipment in roll form.

2. A method of making shaped composite in accordance with claim 1, wherein:

said cellulosic fibrous material comprises wood pulp fibers.

3. A method of making shaped components in accordance with claim 1, wherein:

said step of transversely cutting includes forming non-linear cuts transversely of said subdivided webs.

4. A method of making shaped components in accordance with claim 1, wherein:

adjacent ones of said subdivided webs are juxtaposed and complementary with each other.

5. A method of making shaped components in accordance with claim 1, wherein:

adjacent ones of said subdivided webs are non-complementary, said method including collecting waste material from between adjacent ones of said subdivided webs, and at least partially recycling said waste material for formation of said web of said fibrous material.

6. A method of making shaped components in accordance with claim 1, wherein:

longitudinal slits formed in said web of material during said slitting step are identical.

7. A shaped component for a disposable absorbent article formed in accordance with the method of claim 1.

8. A shaped component in accordance with claim 7, wherein:

said cellulosic fibrous material comprises wood pulp fibers.

* * * * *